United States Patent [19]

Sachtler et al.

[11] Patent Number: 5,081,084
[45] Date of Patent: * Jan. 14, 1992

[54] CATALYST FOR ISOMERIZING ALKYLAROMATICS

[75] Inventors: Johann W. A. Sachtler, Des Plaines; Randy J. Lawson, Palatine; Susan L. Lambert, Rolling Meadows, all of Ill.

[73] Assignee: UOP, Des Plaines, Ill.

[ * ] Notice: The portion of the term of this patent subsequent to Sep. 18, 2007 has been disclaimed.

[21] Appl. No.: 542,611

[22] Filed: Jun. 25, 1990

Related U.S. Application Data

[60] Division of Ser. No. 447,274, Dec. 7, 1989, Pat. No. 4,962,259, which is a continuation-in-part of Ser. No. 281,424, Dec. 8, 1988, Pat. No. 4,886,927, which is a division of Ser. No. 109,019, Oct. 16, 1987, abandoned.

[51] Int. Cl.$^5$ .............................................. B01J 29/32
[52] U.S. Cl. .................................. 502/61; 502/66; 502/71
[58] Field of Search ................... 502/61, 71, 66

[56] References Cited

U.S. PATENT DOCUMENTS

| | | | |
|---|---|---|---|
| 4,482,773 | 11/1984 | Chu et al. | 585/481 |
| 4,485,185 | 11/1984 | Onodera et al. | 502/71 |
| 4,584,423 | 4/1986 | Nacamuli et al. | 585/481 |
| 4,585,641 | 4/1986 | Barri | 423/331 |
| 4,599,475 | 7/1986 | Kresge et al. | 585/481 |
| 4,957,891 | 9/1990 | Sachtler et al. | 502/61 |

FOREIGN PATENT DOCUMENTS 252705  1/1988  European Pat. Off. .............. 502/61

*Primary Examiner*—Carl F. Dees
*Attorney, Agent, or Firm*—Thomas K. McBride; John F. Spears, Jr.; Richard E. Conser

[57] ABSTRACT

This invention presents a novel catalyst formulation for the isomerization of alkylaromatic hydrocarbons. The catalyst is comprised of at least one Group VII metal, and a pentasil zeolite having an x-ray diffraction characteristic of ZSM-12 wherein a portion of the aluminum atoms have been replaced with gallium atoms. When utilized in a process for isomerizing a non-equilibrium mixture of xylenes containing ethylbenzene, a greater yield of para-xylene is obtained compared to prior-art processes.

7 Claims, 2 Drawing Sheets

Paraxylene In Product / Total Xylenes (Mole %)

CATALYST FOR ISOMERIZING ALKYLAROMATICS

CROSS REFERENCE TO RELATED APPLICATIONS

This application is a division of prior copending application Ser. No. 447,274, filed Dec. 7, 1989, now U.S. Pat. No. 4,962,259, which is a continuation-in-part of application Ser. No. 281,424, filed Dec. 8, 1988, now U.S. Pat. No. 4,886,927, which is a division of application Ser. No. 109,019, filed Oct. 16, 1987, now abandoned. The disclosures of these applications are incorporated herein by reference thereto.

FIELD OF THE INVENTION

This invention relates to an improved catalyst for the isomerization of xylenes and conversion of ethylbenzene. More specifically, the invention concerns a catalyst composition comprising a Group VIII metal component and a gallium-substituted pentasil zeolite.

BACKGROUND OF THE INVENTION

The xylenes, namely ortho-xylene, meta-xylene and para-xylene, are important chemicals and find wide and varied application in industry. Ortho-xylene is a reactant for the production of phthalic anhydride. Meta-xylene is used in the manufacture of plasticizers, azo dyes, wood preservers, etc. Para-xylene upon oxidation yields terephthalic acid which is used in the manufacture of synthetic textile fibers.

As a result of the important applications to which the individual xylene isomers are subjected, it is often very important to be able to produce high concentrations of a particular xylene. This can be accomplished by converting a non-equilibrium mixture of the xylene isomers, which mixture is low in the desired xylene isomer, to a mixture which approaches equilibrium concentrations. Various catalysts and processes have been devised to accomplish the isomerization process. For example, it is well known in the art that catalysts such as aluminum chloride, boron fluoride, liquid hydrofluoric acid, and mixtures of hydrofluoric acid and boron fluoride can be used to isomerize xylene mixtures.

Industrially, isomerization of xylenes and conversion of ethylbenzene is performed primarily to produce para-xylene. A typical processing scheme for this objective comprises: (a) separating para-xylene from a $C_8$ alkylaromatic mixture using, for example, molecular sieve technology, to obtain a para-xylene-rich stream and a para-xylene-depleted stream; (b) isomerizing the para-xylene depleted stream to near equilibrium in an isomerization reaction zone; and, (c) recycling the isomerization product to separation along with the fresh $C_8$ alkylaromatic mixture.

The present invention is particularly concerned with the isomerization reaction step which may be used in an overall process directed to para-xylene production. An important parameter to consider in this isomerization reaction step is the degree of approach to xylene equilibrium achieved. It is desirable to run the isomerization process as close to equilibrium as possible in order to maximize the para-xylene yield. However, associated with this is a greater cyclic $C_8$ loss due to side-reactions (cyclic $C_8$ hydrocarbons include xylenes, ethylbenzene, and $C_8$ naphthenes.) The approach to equilibrium that is used is an optimized compromise between high $C_8$ cyclic loss at high conversion (i.e. very close approach to equilibrium) and high utility costs due to the large recycle rate of unconverted ethylbenzene, ortho-xylene, meta-xylene, and $C_8$ naphthenes which result from the hydrogenation of the $C_8$ aromatics. The correlation of cyclic $C_8$ loss versus the distance from xylene equilibrium is a measure of catalyst selectivity. Thus there is a strong incentive to develop a catalyst formulation which minimizes cyclic $C_8$ loss while maximizing para-xylene yield.

Numerous catalysts have been proposed for use in xylene isomerization processes such as mentioned above. More recently, a number of patents have disclosed the use of crystalline aluminosilicate zeolite-containing catalysts for isomerization and conversion of $C_8$ alkylaromatics. Crystalline aluminosilicates generally referred to as zeolites, may be represented by the empirical formula:

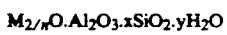

$$M_{2/n}O \cdot Al_2O_3 \cdot xSiO_2 \cdot yH_2O$$

in which n is the valence of M which is generally an element of Group I or II, in particular, lithium, sodium, potassium, magnesium, calcium, strontium, or barium, and x is generally equal to or greater than 2. Zeolites have skeletal structures which are made up of three-dimensional networks of $SiO_4$ and $AlO_4$ tetrahedra, corner-linked to each other by shared oxygen atoms. Zeolites with high $SiO_2/Al_2O_3$ ratios have received much attention as components for isomerization catalysts. Representative of zeolites having such high proportion of $SiO_2$ include mordenite and the ZSM varieties. It is also known in the art that zeolites of the ZSM series can be prepared with gallium atoms substituted for aluminum atoms, for example, see U.S. Pat. No. 4,585,641. In addition to the zeolite component, certain metal promoters and inorganic oxide matrices have been included in isomerization catalyst formulations. Examples of inorganic oxides include silica, alumina, and mixtures thereof. Metal promoters such as Group VIII or Group III metals of the Periodic Table, have been used to provide a dehydrogenation functionality. The acidic function can be supplied by the inorganic oxide matrix, the zeolite, or both.

When employing catalysts containing zeolites for the isomerization of alkylaromatics, characteristics such as acid site strength, zeolite pore diameter, and zeolite surface area become important parameters to consider during formulation development. Variation of these characteristics in a way that reduces side-reactions, such as, transalkylation, is required in order to achieve acceptable levels of cyclic $C_8$ loss.

It has been found that, if a catalyst is formulated with the components, and in the manner set forth hereinafter, an improved process for the conversion of a non-equilibrium mixture of xylenes containing ethylbenzene is obtained.

OBJECTS AND EMBODIMENTS

A principal object of the present invention is to provide a novel catalyst for the isomerization of isomerizable hydrocarbons. More specifically, the instant invention is aimed at a catalyst composition which, when utilized for the isomerization of alkylaromatic hydrocarbons, results in minimal loss of the alkylaromatic hydrocarbons. Other objects of the instant invention are to present a method of preparation and a process use of the catalyst.

Accordingly, a broad embodiment of the invention is directed toward a catalyst for the isomerization of isomerizable hydrocarbons comprising at least one Group VIII metal component, and a gallium-substituted pentasil zeolite. A preferred pentasil zeolite is a zeolite having an x-ray diffraction characteristic of ZSM-12.

Another embodiment is directed toward a process for the isomerization of a feed stream comprising a non-equilibrium mixture of xylenes containing ethylbenzene, which comprises contacting the feed in the presence of hydrogen at a temperature of from about 300° to 500° C., a pressure of from about 69 to about 6895 kPa (ga), a liquid hourly space velocity of from about 0.5 to about 10 hr$^{-1}$ with a catalyst comprising at least one Group VIII metal component and a gallium-substituted pentasil zeolite having an x-ray diffraction characteristic of ZSM-12.

These as well as other objects and embodiments will become evident from the following more detailed description of the invention.

INFORMATION DISCLOSURE

The prior art recognizes numerous isomerization processes employing a variety of catalyst formulations. However, it is believed that none of the prior art processes recognizes the use of the catalyst formulation and method of making same which forms an integral part of the instant invention.

U.S. Pat. No. 3,923,639 (Ciric) is directed to a hydrocarbon cracking process utilizing a catalyst composition comprising a crystalline aluminosilicate ZSM-4 zeolite. Although the reference lists as possible components Group VIII metals and a variety of matrix materials, the reference is silent as to the utility of a gallium-substituted pentasil in combination with a Group VIII metal for the isomerization of alkylaromatic hydrocarbons.

The conversion of heavy reformate using a variety of different catalyst compositions, including silica-alumina containing pentasil zeolites, is taught in U.S. Pat. No. 4,066,531 (Owen et al). However, the reference is not cognizant of the utility of a gallium-substituted pentasil zeolite in combination with the other components of the instant invention.

U.S. Pat. No. 4,255,288 (Cull et al) teaches a catalyst comprising a Y-type zeolite, alumina, zirconia, and at least one each of Group VIB and Group VIII metals. Hydrocracking and hydrodesulfurization tests show superior results for catalysts of the invention. The reference does not disclose a gallium-substituted pentasil zeolite.

Several relevant references are directed to processes and catalyst compositions specifically for isomerizing alkylaromatics. Related U.S. Pat. Nos. 4,331,822 and 4,485,185 (Onodera et al) teach the use of a catalyst containing silica-alumina pentasil zeolites having added thereto platinum and a second metal. However, neither reference recognizes gallium-substituted pentasil zeolites. U.S. Pat. No. 4,482,773 (Chu et al) is directed to a process for isomerizing a mixture of xylenes and ethylbenzene with a ZSM-5 catalyst containing platinum and a Group IIA component. However, the reference does not recognize the utility of gallium substitution in the zeolite. Another reference, U.S. Pat. No. 4,584,423 (Nacamuli et al), teaches a process for isomerizing a non-equilibrium mixture of xylenes containing ethylbenzene in the absence of hydrogen using a catalyst containing ZSM-5 or ZSM-11 wherein gallium may be substituted for aluminum. This reference makes no mention of the utility of a Group VIII metal.

U.S. Pat. No. 4,599,475 (Kresge et al) teaches an isomerization process using a catalyst comprising ZSM-23 zeolite. Kresge et al disclose gallium among a broad range of nine "Y" framework elements and alumina among a non-limiting list of seven binder materials. However, Kresge et al teach away from the use of a larger-pore zeolite than ZSM-23 in the disclosed range of framework and binder elements.

In summary, it appears that the prior art only generally recognizes that zeolites have utility for isomerization of isomerizable alkylaromatics and that no single reference teaches nor suggests the invention claimed herein.

DETAILED DESCRIPTION OF THE INVENTION

Figure 1:
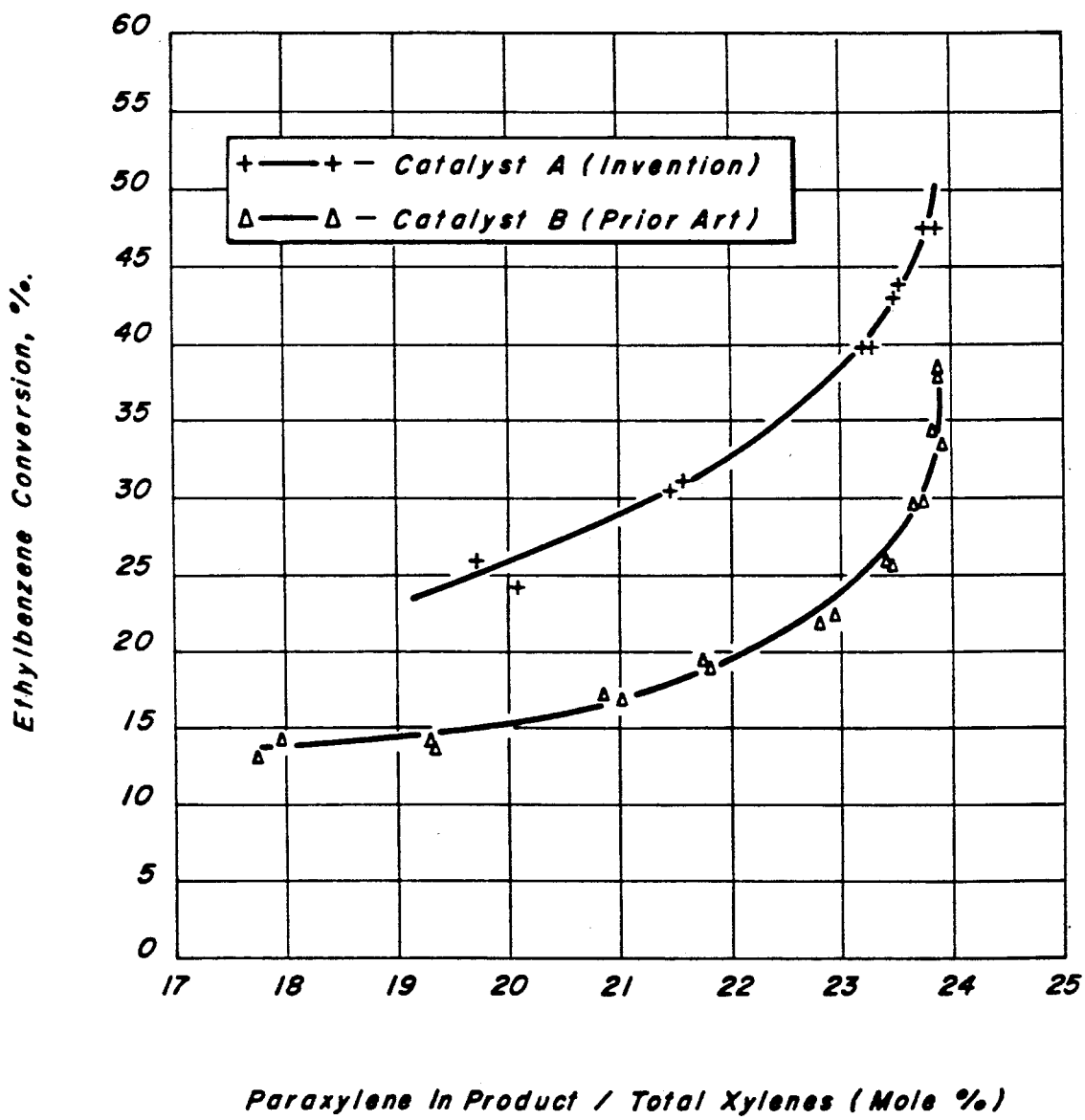
FIG. 1 compares the performance of Catalyst A of the invention and Catalyst B of the prior art, relating ethylbenzene conversion to the paraxylene content of the xylenes product.

As mentioned above, this invention is concerned with a catalyst composition useful for the isomerization and conversion of a non-equilibrium mixture of $C_8$ aromatic hydrocarbons. This catalytic composite comprises at least one Group VIII metal component, and a pentasil zeolite having an x-ray diffraction characteristic of ZSM-12 wherein a portion of aluminum atoms have been replaced with gallium atoms. When utilized in a process for isomerizing a non-equilibrium mixture of alkylaromatics, the instant invention allows for a closer approach to xylene equilibrium resulting in a greater yield of para-xylene without the high loss of $C_8$ aromatics common to prior art processes.

The catalyst of the instant invention contains at least one Group VIII metal component of the Periodic Table (see, Cotton and Wilkinson, *Advanced Inorganic Chemistry* (3rd Ed., 1972)). Preferably, this Group VIII metal is selected from the platinum group metals. Of the platinum group metals, which include palladium, rhodium, ruthenium, osmium and iridium, the use of platinum is preferred. The platinum group component may exist within the final catalyst composite as a compound such as an oxide, sulfide, halide, oxysulfide, etc., or as an elemental metal or in combination with one or more other ingredients of the catalyst. It is believed that the best results are obtained when substantially all the platinum group component exists in the elemental state. The platinum group component generally comprises from about 0.01 to about 2 wt. % of the final catalytic composite, calculated on an elemental basis. It is preferred that the platinum content of the catalyst be between about 0.1 and 1 wt. %. The preferred platinum group component is platinum, with palladium being the next preferred metal. The platinum group component may be incorporated into the catalyst composite in any suitable manner such as by coprecipitation or cogelation with the inorganic-oxide matrix, or by ion-exchange or impregnation of the zeolite, or by ion-exchange or impregnation of the zeolite and matrix composite. The preferred method of preparing the catalyst normally involves the utilization of a water-soluble, decomposable compound of a platinum group metal to impregnate the composite. For example, the platinum group component may be added to the composite by commingling the composite with an aqueous solution of chloroplatinic or chloropalladic acid. An acid such as hydrogen chloride is generally added to the impregnation solution to aid in the distribution of the platinum group component through the composite particles.

After addition of the Group VIII metal component to the zeolite and matrix composite, the resultant composite is dried at a temperature ranging from about 100° to about 200° C. for a period of at least 2 to about 24 hours or more, and finally calcined or oxidized at a temperature ranging from about 450° to about 650° C. in air or oxygen atmosphere for a period of about 0.5 to about 10 hours in order to convert all of the metallic components to the corresponding oxide form. The resultant oxidized composite is preferably subjected to a substantially water-free reduction step prior to its use in the isomerization of hydrocarbons. This step is designed to selectively reduce the Group VIII metal component to the elemental metallic state and to ensure a uniform and finely divided dispersion of the metallic component throughout the catalyst. Preferably, a substantially pure and dry hydrogen stream (i.e. less than 20 vol. ppm $H_2O$) is used as the reducing agent in this step. The reducing agent is contacted with the oxidized catalyst at conditions including a reduction temperature ranging from about 200° to about 650° C. and a period of time of about 0.5 to 10 hours effective to reduce substantially all of the Group VIII metal component to the elemental metallic state.

The resulting reduced catalytic composite may, in some cases, be beneficially subjected to a presulfiding operation designed to incorporate in the catalytic composite from about 0.05 to about 0.5 wt. % sulfur calculated on an elemental basis. Preferably, this presulfiding treatment takes place in the presence of hydrogen and a suitable sulfur-containing compound such as hydrogen sulfide, lower molecular weight mercaptans, organic sulfides, etc. Typically, this procedure comprises treating the reduced catalyst with a sulfiding gas such as a mixture of hydrogen and hydrogen sulfide having about 10 moles of hydrogen per mole of hydrogen sulfide at conditions sufficient to effect the desired incorporation of sulfur, generally including a temperature ranging from about 10° up to about 593° C. or more. It is generally a good practice to perform this presulfiding step operation under substantially water-free conditions.

The gallium-substituted pentasil zeolite utilized in the instant invention preferably has a formula (expressed in terms of mole ratios of oxides) as follows:

$$M_{2/n}O:W_2O_3:ySiO_2:zH_2O$$

wherein M is at least one cation of valence n, W is gallium and/or aluminum, y is at least 5, preferably at least 12, and z is from 0 to 40. The zeolite preferably has an X-ray diffraction characteristic of pentasil zeolites, which includes ZSM-5, ZSM-8, ZSM-11, ZSM-12, ZSM-23, and ZSM-35, with ZSM-12 being particularly preferred. "Pentasil" is a term used to describe a class of shape-selective zeolites. This novel class of zeolites is well known to the art and is typically characterized by a silica/alumina mole ratio of at least about 12. Suitable descriptions of the pentasils may be found in U.S. Pat. Nos. 4,159,282; 4,163,018; and 4,278,565, all of which are incorporated herein by reference. The zeolite framework may contain only gallium and silicon atoms or may contain a combination of gallium, aluminum, and silicon atoms. The gallium content, expressed as mole ratios of $SiO_2/Ga_2O_3$, may range from 20:1 to 400:1. The preferred gallium-substituted pentasil zeolite has a ZSM-12 structure with a gallium content ranging from 0.1 to 10 wt. % of the zeolite, most preferably ranging from 0.5 to 5 wt. %. The gallium-substituted pentasil zeolite may be prepared by crystallization from a reaction mixture comprising a silica source, a source of $Ga_2O_3$, a source of $Al_2O_3$ if desired, and optionally an organic template compound. It is believed that the preparation of zeolites is within the competence of one skilled in the art and a particular preparation method is not critical to the instant invention. It is preferred that the catalyst of the instant invention contain from 1 to 20 wt. % gallium-substituted ZSM-12 zeolite. In a preferred embodiment, the catalyst comprises an inorganic-oxide matrix.

The inorganic oxide matrix utilized in the present invention preferably is a porous, adsorptive, high-surface area support having a surface area of about 25 to about 500 m$^2$/g. The matrix should also be uniform in composition and relatively refractory to the conditions utilized in the hydrocarbon conversion process. By the term "uniform in composition", it is meant that the support be unlayered, has no concentration gradients of the species inherent to its composition, and is completely homogeneous in composition. Thus, if the support is a mixture of two or more refractory materials, the relative amounts of these materials will be constant and uniform throughout the entire support. It is intended to include within the scope of the present invention matrix materials known in the art such as: (1) activated carbon, coke, or charcoal; (2) silica or silica gel, silicon carbide, clays and silicates including those synthetically prepared and naturally occurring, which may or may not be acid treated, for example, attapulgus clay, diatomaceous earth, fuller's earth, kaolin, kieselguhr, etc.; (3) ceramics, porcelain, bauxite; (4) refractory inorganic oxides such as alumina, titanium dioxide, zirconium dioxide, chromium oxide, zinc oxide, magnesia, thoria, boria, silica-alumina, silica-magnesia, chromia-alumina, alumina-boria, silica-zirconia, zirconia-alumina, etc.; and (5) combinations of one or more elements from one or more of these groups. The preferred matrices for use in the present invention are refractory inorganic oxides, with best results obtained with a binder comprised of alumina. Suitable aluminas are the crystalline aluminas known as the gamma-, eta-, and theta-aluminas. Excellent results are obtained with a matrix of substantially pure gamma-alumina. In addition, in some embodiments, the alumina matrix may contain minor proportions of other well known refractory inorganic oxides such as silica, zirconia, magnesia, etc. The preferred combination of inorganic oxides is zirconia with gamma- or eta-alumina, especially from about 90 to 99 wt % alumina and from about 1 to 10 wt % zirconia. Matrices preferably have an apparent bulk density of about 0.3 to about 0.8 g/cc and surface area characteristics such that the average pore diameter is about 20 to 300 angstroms and the pore volume is about 0.1 to about 1 cc/g. Preferably the matrix is uniform in composition, may be prepared in any suitable manner, and may be synthetically prepared or naturally occurring. Whichever type of matrix is employed, it may be activated prior to use by one or more treatments including but not limited to drying, calcination, and steaming.

Using techniques commonly known to those skilled in the art, the catalyst of the instant invention may be composited and shaped into any useful form such as spheres, pills, cakes, extrudates, powders, granules, tablets, etc., and utilized in any desired size. These shapes may be prepared utilizing any known forming operations including spray drying, tabletting, spherizing, extrusion, and nodulizing. A preferred shape for the catalyst composite is the extrudate prepared using the well-known extrusion method. Here the pentasil zeolite with or without metallic components added is combined with the binder and a suitable peptizing agent and mixed to form a homogeneous dough or thick paste. This material is then extruded through a die pierced with multiple holes and the spaghetti-shaped extrudate is cut off on the opposite side to form short cylinders. The rheological properties of the dough mixture can be varied by the use of "extrusion aids" such as methylcellulose, stearates, small amounts of clay, colloidal silica, etc. After extrusion, the cylinders are dried and calcined as set forth hereinbelow.

An alternative shape of the composite is a sphere, continuously manufactured by the well-known oil drop method. Preferably, this method involves dropping the mixture of zeolite, alumina sol, and gelling agent into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics.

The resulting aged and gelled particles are then washed and dried at a relatively low temperature of about 50°-200° C. and subjected to a calcination procedure at a temperature of about 450°-700° C. for a period of about 1 to about 20 hours. This treatment effects conversion of the hydrogel to the corresponding alumina matrix. In a preferred embodiment, the calcined composite is washed to remove any remaining alkali metal cations that may be present. The wash solution is preferably an aqueous ammonium solution, most preferably containing about 0.5% $NH_3$ in water. After washing at about 95° C., the composite is dried at about 110° C. See the teachings of U.S. Pat. No. 2,620,314 for additional details.

The process of this invention is applicable to the isomerization of isomerizable alkylaromatic hydrocarbons of the general formula:

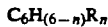

$$C_6H_{(6-n)}R_n$$

where n is an integer from 2 to 5 and R is $CH_3$, $C_2H_5$, $C_3H_7$, or $C_4H_9$, in any combination and including all the isomers thereof. Suitable alkylaromatic hydrocarbons include, for example, ortho-xylene, meta-xylene, para-xylene, ethylbenzene, ethyltoluenes, the trimethylbenzenes, the diethylbenzenes, the triethylbenzenes, methylpropylbenzenes, ethylpropylbenzenes, the diisopropylbenzenes, and mixtures thereof.

It is contemplated that any aromatic $C_8$ mixture containing ethylbenzene and xylene may be used as feed to the process of this invention. Generally, such mixture will have an ethylbenzene content in the approximate range of 5 to 50 wt. %, an ortho-xylene content in the approximate range of 0 to 35 wt. %, a meta-xylene content in the approximate range of 20 to 95 wt. % and a para-xylene content in the approximate range of 0 to 15 wt. %. It is preferred that the aforementioned $C_8$ aromatics comprise a non-equilibrium mixture. The feed to the instant process, in addition to $C_8$ aromatics, may contain nonaromatic hydrocarbons, i.e. naphthenes and paraffins in an amount up to 30 wt. %.

The alkylaromatic hydrocarbons for isomerization may be utilized as found in selective fractions from various refinery petroleum streams, e.g., as individual components or as certain boiling range fractions obtained by the selective fractionation and distillation of catalytically cracked gas oil. The process of this invention may be utilized for conversion of isomerizable aromatic hydrocarbons when they are present in minor quantities in various streams. The isomerizable aromatic hydrocarbons which may be used in the process of this invention need not be concentrated. The process of this invention allows the isomerization of alkylaromatic containing streams such as reformate to produce specified xylene isomers, particularly para-xylene, thus upgrading the reformate from its gasoline value to a high petrochemical value.

According to the process of the present invention, an alkylaromatic hydrocarbon charge stock, preferably in admixture with hydrogen, is contacted with a catalyst of the type hereinabove described in an alkylaromatic hydrocarbon isomerization zone. Contacting may be effected using the catalyst in a fixed bed system, a moving bed system, a fluidized bed system, or in a batch-type operation. In view of the danger of attrition loss of the valuable catalyst and of operational advantages, it is preferred to use a fixed bed system. In this system, a hydrogen-rich gas and the charge stock are preheated by suitable heating means to the desired reaction temperature and then passed into an isomerization zone containing a fixed bed of catalyst. The conversion zone may be one or more separate reactors with suitable means therebetween to ensure that the desired isomerization temperature is maintained at the entrance to each zone. It is to be noted that the reactants may be contacted with the catalyst bed in either upward, downward, or radial flow fashion, and that the reactants may be in the liquid phase, a mixed liquid-vapor phase, or a vapor phase when contacted with the catalyst.

The process of this invention for isomerizing an isomerizable alkylaromatic hydrocarbon is preferably effected by contacting the alkylaromatic, in a reaction zone containing an isomerization catalyst as hereinafter described, with a fixed catalyst bed by passing the hydrocarbon in a down-flow or radial flow fashion through the bed, while maintaining the zone at proper alkylaromatic isomerization conditions such as a temperature in the range from about 0°-600° C. or more, and a pressure of about 101 kPa (abs) to about 10,340 kPa (ga) or more. Preferably, the operating temperature ranges from about 300°-500° C. and the pressure ranges from about 69 to about 6,895 kPa (ga). The hydrocarbon is passed, preferably, in admixture with hydrogen at a hydrogen/hydrocarbon mole ratio of about 0.5:1 to about 25:1 or more, and at a liquid hourly hydrocarbon space velocity of about 0.1 to about 20 $hr^{-1}$ or more, most preferably at 0.5 to 10 $hr^{-1}$. Other inert diluents such as nitrogen, argon, etc., may be present.

The particular product recovery scheme employed is not deemed to be critical to the instant invention. Any recovery scheme known in the art may be used. Typically, the reactor effluent will be condensed with the hydrogen and light hydrocarbon components removed therefrom by flash separation. The condensed liquid product is then subject to a fractionation procedure to further purify the desired liquid product. In some instances, it may be desirable to recover certain product species, such as ortho-xylene, by selective fractionation. In most instances, the liquid xylene product is processed to selectively recover the para-xylene isomer. Recovery of para-xylene can be performed by crystallization methods or most preferably by selective adsorption using crystalline aluminosilicates.

The following examples are presented for purpose of illustration only and are not intended to limit the scope of the present invention.

EXAMPLES

The examples present test results obtained when catalysts of the invention were evaluated in an isomerization process. The catalysts were evaluated using a pilot plant flow reactor processing a non-equilibrium $C_8$ aromatic feed comprising 52.0 wt. % meta-xylene, 18.5 wt. % ortho-xylene, 0.1 wt. % para-xylene, 21.3 wt. % ethylbenzene, and 0.1 wt. % toluene, with the balance being nonaromatic hydrocarbons. This feed was contacted with 100 cc of catalyst at a liquid hourly space velocity of 2, and a hydrogen/hydrocarbon mole ratio of 4. Reactor pressure and temperature were adjusted to cover a range of conversion values in order to develop the relationship between $C_8$ ring loss and approach to xylene equilibrium (as determined by product para-xylene to total xylene mole ratio). At the same time, at each temperature, the pressure was chosen to maintain a constant mole ratio of $C_8$ naphthenes to $C_8$ aromatics of approximately 0.06.

EXAMPLE I

Gallium-substituted pentasil zeolite having an x-ray diffraction characteristic of ZSM-12 was prepared for a catalyst of the invention designated as Catalyst A from a template, sodium gallate, and a silica source. The sodium gallate in solution was added slowly to a solution of the template, triethylmethylammonium bromide, in deionized water. The silica source, Ludox AS-40, then was added slowly to the template/gallate solution. The weight ratio of Ludox-40 to template was about 3:1. Hydrothermal crystallization was effected under autogenous pressure at about 150° C. for 20 days, and the solids obtained were filtered, washed with deionized water and dried at 100° C.

A quantity of gallium-substituted pentasil zeolite having an X-ray diffraction pattern equivalent to that of ZSM-5 was prepared for a catalyst of the prior art designated as Catalyst B by adding a silica source, Ludox HS-40, to an aqueous solution containing an organic template, tetrapropylammonium bromide. The weight ratio of silica to template was about 1:1. A solution of sodium gallate was added to the silica and template mixture in an amount to give about 1.0 wt. % gallium based on the finished zeolite. The resultant mixture was autoclaved at about 150° C. for approximately 140 hours. The zeolite obtained was washed, filtered and dried to yield a gallium-substituted pentasil zeolite containing approximately 1.3 wt. % Ga.

Catalysts A and B respectively, were prepared by combining a quantity of each of the above zeolites sufficient to provide a zeolite content of 4.5 wt. % in the finished catalyst with gamma-alumina ground to less than 30 mesh, deionized water, concentrated $HNO_3$ and extrusion aids to form an extrudable mixture. The composites were extruded, air dried at about 110° C. and then calcined at a temperature of about 650° C. After calcination, each of the composites was washed with aqueous ammonia solution, oven dried at 110° C., and reoxidized in dry air at about 565° C.

The extrudates next were impregnated with a solution of chloroplatinic acid containing 4 wt. % hydrochloric acid (based on the calcined spheres) to yield a final platinum concentration as shown. The impregnated spheres were oxidized and chloride adjusted at 525° C., reduced in molecular hydrogen at 565° C., and then sulfided with hydrogen sulfide at ambient temperature to a target sulfur level of 0.1 wt. %. The two extrudates had the following approximate analysis:

|  | Catalyst A (Invention) | Catalyst B (Prior Art) |
| --- | --- | --- |
| Apparent bulk density, g/cc | 0.453 | 0.485 |
| Platinum, wt. % | 0.38 | 0.35 |
| Chloride, wt. % | 0.70 | 0.52 |
| Sulfur, wt. % | 0.08 | 0.17 |

Note that the platinum contents were adjusted in relation to apparent bulk density to be essentially the same on a volume basis for experimental comparison purposes.

EXAMPLE II

The performance of Catalysts A and B for isomerization of xylenes and ethylbenzene was compared using the non-equilibrium $C_8$ aromatic feed and test conditions described hereinabove.

FIG. 1 shows the conversion of ethylbenzene as a function of para-xylene in the total xylenes. Para-xylene in total xylenes represents the approach to equilibrium para-xylene content, and is used as a measure of xylene-isomerization severity. Ethylbenzene conversion is industrially important because ethylbenzene typically comprises a significant portion of $C_8$-aromatic streams. Due to the close boiling points of ethylbenzene and the xylenes, it is very difficult and costly to remove ethylbenzene by fractionation. However, it must be excluded in order to prevent its build-up in the separation/isomerization loop described hereinbelow. The most preferred method for removing ethylbenzene is isomerization to para-xylene. It is well known in the art that isomerization of ethylbenzene to xylenes is more difficult than interconversion of the three xylene isomers, and therefore activity for ethylbenzene isomerization is a critical catalyst property. As is shown in FIG. 1, the ethylbenzene conversion of Catalyst A of the invention is significantly greater, at any level of xylene-isomerization severity, than of Catalyst B of the prior art.

At constant conversion, data indicate that the $C_8$ ring loss for Catalyst A is 0.5-1 mole-% higher than for Catalyst B. This may be offset industrially by reducing the levels of ethylbenzene conversion and xylene isomerization severity to limit the $C_8$ ring loss. Thus, for a complete evaluation of catalyst performance, the effects of ethylbenzene conversion, xylene isomerization severity, and $C_8$ ring loss on the combined para-xylene separation and isomerization processes should be considered. This can be done by relating the recycle ratio and para-xylene yield, as defined in the following.

In the separation/isomerization process combination, fresh $C_8$-aromatic feed is combined with $C_8$-aromatics and naphthenes from the isomerization reaction zone and fed to the para-xylene separation zone; the para-xylene depleted stream is fed to the isomerization reaction zone, where the $C_8$-aromatic isomers are again isomerized to near-equilibrium levels. In this process scheme the $C_8$-aromatic isomers are recycled to extinction, until they are either converted to para-xylene or lost due to side-reactions. The presence of a $C_8$-naphthene stream throughout the process is necessary to provide the intermediates required for ethylbenzene isomerization in the isomerization reaction zone. The para-xylene yield for the process is defined as the weight fraction of the fresh $C_8$-aromatic feed that is ultimately converted to the para-xylene product stream. The recycle ratio is defined as the weight ratio of rate of recycle of $C_8$-aromatics+naphthenes from the isomerization reaction zone to the rate of fresh $C_8$-aromatic feed addition to the process. In a graph of para-xylene yield versus recycle ratio, superior catalyst performance is readily distinguished as superior para-xylene yield at a given recycle ratio. Industrially, operating conditions are a balance between desirable high para-xylene yield and undesirable utility costs that increase with recycle ratio.

Figure 2:
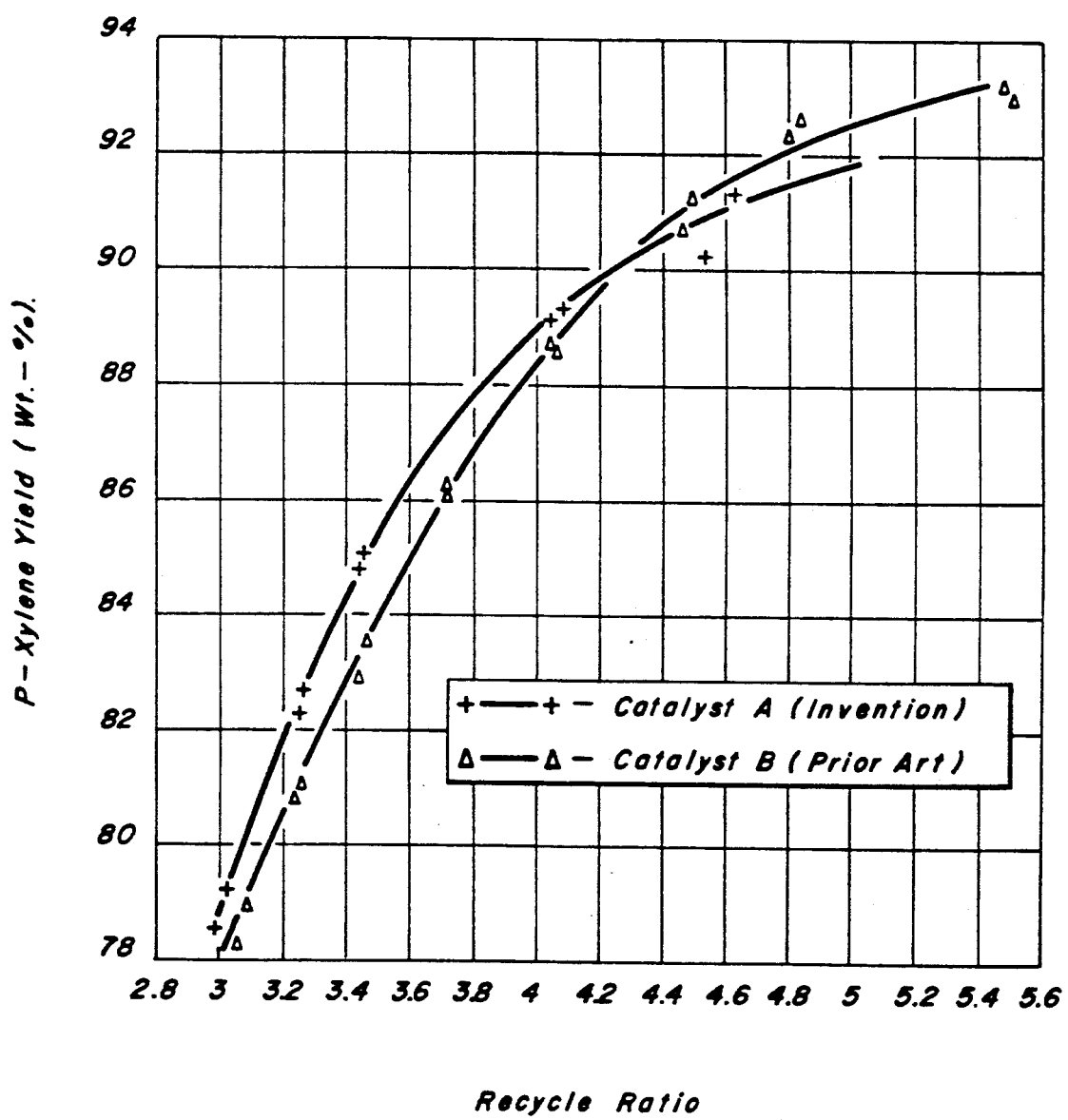
FIG. 2 compares the performance of Catalysts A and B of the invention and prior art, respectively, by relating para-xylene yield to the ratio of $C_8$ cyclics recycled from the isomerization reactor to the para-xylene separation zone.

The results for Catalysts A and B are shown in FIG. 2. It is evident from the Figure that at low recycle ratios, at which utility costs are minimized, Catalyst A of the invention provides a higher para-xylene yield than the prior art Catalyst B. Stated differently, these calculations show that at low recycle ratios, the high ethylbenzene conversion of the catalyst of this invention outweighs the increase in $C_8$ ring loss at constant conversion over the prior art Catalyst B, thus providing an improved overall process.

We claim:

1. A catalyst for the isomerization of isomerizable alkylaromatic hydrocarbons comprising a platinum component and a gallium-substituted pentasil zeolite having an x-ray diffraction pattern characteristic of ZSM-12, and an inorganic-oxide matrix.

2. The catalyst of claim 1 further characterized in that the platinum component comprises from about 0.1 to 1 wt. % platinum on an elemental basis.

3. The catalyst of claim 1 further characterized in that the zeolite contains from about 0.1 to 10 wt. % gallium.

4. The catalyst of claim 1 further characterized in that the catalyst comprises 0.05 to about 0.5 wt. % sulfur calculated as elemental sulfur.

5. The catalyst of claim 1 further comprising an inorganic-oxide matrix.

6. The catalyst of claim 5 wherein the inorganic-oxide matrix comprises alumina.

7. A catalyst for the isomerization of a non-equilibrium mixture of xylenes containing ethylbenzene comprising 0.1 to 5 wt. % platinum, a gallium-substituted pentasil zeolite having an x-ray diffraction pattern characteristic of ZSM-12 and an alumina matrix.

* * * * *